United States Patent [19]

Scotese et al.

[11] 4,215,123

[45] Jul. 29, 1980

[54] ANTISECRETORY 4-OXY-3-CARBOXY OR CYANO-1,2-DIHYDRO-2-OXO-1,8-NAPHTHYRIDINE DERIVATIVES

[75] Inventors: Anthony C. Scotese, King of Prussia; Arthur A. Santilli, Havertown, both of Pa.

[73] Assignee: American Home Products Corporation, New York, N.Y.

[21] Appl. No.: 36,921

[22] Filed: May 7, 1979

[51] Int. Cl.$^2$ .............................................. A61K 31/435
[52] U.S. Cl. .................................................. 424/256
[58] Field of Search ......................................... 424/256

[56] References Cited

U.S. PATENT DOCUMENTS 3,838,120  9/1974  Zalay et al. ................. 260/244 R
4,128,649  12/1978  Hardtmann .................. 424/256

FOREIGN PATENT DOCUMENTS 851866  8/1977  Belgium ......................... 424/263

OTHER PUBLICATIONS

Derwent–Farm Doc 47527v of Dt 2,360,329.
Derwent–Farm Doc 80383y of J. 2,116,495.

*Primary Examiner*—Frederick E. Waddell
*Attorney, Agent, or Firm*—Richard K. Jackson

[57] ABSTRACT

Substituted 4-oxy-3-carboxy or cyano-1,2-dihydro-2-oxo-1,8-naphthyridine derivatives as gastric antisecretory agents for use in the treatment of peptic ulcer disease.

17 Claims, No Drawings

ANTISECRETORY 4-OXY-3-CARBOXY OR CYANO-1,2-DIHYDRO-2-OXO-1,8-NAPHTHYRIDINE DERIVATIVES

BRIEF DESCRIPTION OF THE INVENTION

In accordance with this invention there is provided a process for treating peptic ulcer disease which comprises administering to an animal suffering from peptic ulcers, a substituted 4-oxy-3-carboxy or cyano-1,2-dihydro-2-oxo-1,8-naphthyridine derivative.

The anti-ulcer agents of this invention function as anti-secretory agents to reduce (1) total gastric volume, (2) hydrogen ion secretion, or (3) hydrogen ion concentration. The reduction of any one of these parameters aids in attenuating the general debilitating influence of a peptic ulcer. The use of compounds exhibiting anti-secretory activity in the curative and/or prophylactic treatment of peptic ulcer disease is an established, beneficial procedure.

DETAILED DESCRIPTION OF THE INVENTION

The anti-secretory agents useful in the process of this invention are of the formula:

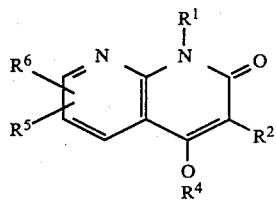

in which
- $R^1$ is hydrogen, alkyl of 1 to 6 carbon atoms, aralkyl of 7 to 9 carbon atoms, or alken-(3,4,5 or 6)-yl of 3 to 6 carbon atoms;
- $R^2$ is hydrogen, alkoxycarbonyl of 2 to 7 carbon atoms; carboxy, carbamyl, N-alkylcarbamyl of 2 to 7 carbon atoms, N-alkoxyethylcarbamyl of 4 to 9 carbon atoms, hydrazido or cyano;
- $R^4$ is hydrogen, alkyl of 1 to 6 carbon atoms;
- $R^5$ and $R^6$ are independently hydrogen or alkyl of 1 to 6 carbon atoms or a pharmaceutically acceptable alkali metal salt thereof.

By pharmaceutically acceptable alkali metal salts, applicants intend to embrace the sodium and potassium salts of the 4-hydroxy substituted 1,8-naphthyridine derivatives.

The antisecretory agents disclosed herein are produced by conventional techniques from known materials or compounds readily preparable by the medicinal chemist.

Each of the anti-secretory agents disclosed was found active in the following scientifically recognized, standard test for anti-secretory activity:

Male Charles River rats of Sprague-Dawley strain and 190 to 240 gm. body weight are food deprived for 24 hours with water ad libitum until the test. Groups of ten rats each are assigned to either control or drug treatment. Pyloric ligation was performed under ether anesthesia through a midline laparotomy, and either control vehicle (0.25 methylcellulose) or drug in control vehicle was administered intraduodenally. The rats are sacrificed by $CO_2$ asphyxiation four hours after pyloric ligation. The stomachs are removed and the gastric contents emptied into graduated centrifuge tubes. The gastric samples are centrifuged for 20 minutes and those obviously contaminated by food, blood, or feces are discarded. The volume of gastric fluid is recorded and the acid concentration of 1.0 ml. sample aliquots is measured by electrometric titration to pH 7.0 with 0.1 N NaOH. The calculated product of gastric volume (ml/4 hr) and acid concentration (mEq/L) estimates the total acid output (TAO, mEq/4 hr) over the four-hour test period. An analysis of variance is performed on these data to determine statistically significant ($p < 0.05$) deviation between control versus drug-treated groups.

The dosage regimen for therapeutic use of the antisecretory agents disclosed herein will vary with the mode of administration, size and age of the person under treatment as well as the severity of the dysfunction. Therefore, treatment of peptic ulcer disease must be individualized for the patient under the guidance of the attending physician.

The compounds of this invention may be administered by conventional oral or parenteral routes as solids, liquids or isotonic solutions. Conventional adjuvants known to the art may be combined with the compounds disclosed herein to provide compositions and solutions for administration purposes although it is considered desirable and feasible to use the compounds neat or pure without additives other than for the purpose of providing suitable pharmaceutically acceptable solid or liquid dosage unit forms.

The following examples illustrate several techniques applicable in the preparation of the anti-secretory agents of this invention. An index of gastric anti-secretory activity is reported at the end of each example illustrating the production of a compound disclosed herein. The activity is expressed as percentage inhibition of acid secretion in drug treated animals in comparison to control animals based upon intraduodenal (i.d.) administration of 32 mg/kg of the tested compound, unless indicated otherwise.

EXAMPLE 1

1-Ethyl-1,2-dihydro-4-hydroxy-7-methyl-2-oxo-1,8-naphthyridine-3-carboxylic acid ethyl ester A mixture of 26 g. of 2-hydroxy-6-methylnicotinic acid methyl ester obtained by the procedure of Mariella et al., J.A.C.S., 74, 1915 (1952) in 200 ml. of phosphorus oxychloride was heated under reflux for 6 hours. The phosphorus oxychloride was removed in a rotary evaporator and the residue was poured onto 1 liter of cracked ice. The mixture was extracted with 250 ml. of diethyl ether. The ether was dried over magnesium sulfate, filtered and removed in a rotary evaporator to afford 18.0 g. of pure 2-chloro-6-methylnicotinic acid methyl ester.

Anal. Calcd. for $C_8H_8NClO_2$: C, 51.77; H, 4.34; N, 7.55. Found: C, 51.67; H, 4.08; N, 7.34.

To a cold solution of 5.4 g. (0.12 mole) of anhydrous ethyl amine in 5 ml. of ethanol was added 11.1 g. (0.06 mole) of 2-chloro-6-methylnicotinic acid methyl ester. The mixture was heated in a glass autoclave over a steam bath for 5 hours. The mixture was then evaporated in a rotary evaporator and the residue was added to 100 ml. of water and was basified with concentrated ammonium hydroxide. The mixture was then extracted with 100 ml. of chloroform. The chloroform layer was dried over magnesium sulfate, filtered and was evaporated to give 2-ethylamino-6-methylnicotinic acid methyl ester as an oil which was used without further purification.

For characterization purposes, a hydrochloride was prepared by dissolving a few ml. of free base in ethyl acetate and adding dropwise a saturated solution of hydrogen chloride in diethyl ether. A few drops of ethanol was added. The solid which formed was removed by filtration and recrystallized from ethyl acetate-ethanol and dried in vacuo at 56° (m.p. 123°–125° C.).

Anal. Calcd. for $C_{10}H_{15}ClN_2O_2$: C, 52.06; H, 6.12; N, 12.15. Found: 51.69; H, 6.44; N, 12.00.

To a solution of 3.98 g. (0.02 mole) of 2-ethylamino-6-methylnicotinic acid methyl ester in 50 ml. of anhydrous diethyl ether was added 1.5 g. (0.01 mole) of ethyl malonyl chloride. The mixture was stirred at room temperature for 1 hour. The mixture was filtered and the filtrate was evaporated in a rotary evaporator. The residue was added to a solution of 0.23 g. of sodium in 50 ml. of absolute ethanol and was warmed for 5 minutes. The mixture was cooled and the insoluble material was collected and was dissolved in water. Acidification of the water solution with glacial acetic acid afforded a precipitate which was collected, air dried and was recrystallized from heptane to give 1.2 g. of product, m.p. 147°–151° C.

Anal. Calcd. for $C_{14}H_{16}N_2O_4$: C, 60.86; H, 5.84; N, 10.14 Found: C, 60.88; H, 6.00; N, 9.99.

Precentage inhibition—50%

EXAMPLE 2

1-Ethyl-1,2-dihydro-4-hydroxy-7-methyl-2-oxo-1,8-naphthyridine-3-carboxylic acid ethyl ester A stirred mixture of 12 g. of 2-hydroxy-6-methylnicotinic acid in 100 ml. of phosphorus oxychloride was heated under reflux for 3 hours. The phosphorus oxychloride was removed in a rotary evaporator and the residue was poured onto 500 ml. of ice. The mixture was stirred at room temperature for 3 hours and was filtered. The filter cake was collected, air dried and was recrystallized from ethyl acetate to give 7.0 g. of 2-chloro-6-methylnicotinic acid, m.p. 158°–60° C. (Ref. Zalay et al., U.S. Pat. No. 3,838,120; m.p. 142°–9° C.

A mixture of 7 g. of 2-chloro-6-methylnicotinic acid in 100 ml. of 60% aqueous ethylamine was heated in an autoclave in a steam bath for 24 hours. The solution was evaporated in a rotary evaporator and the residue was dissolved in 150 ml. of benzene and this solution was evaporated in a rotary evaporator. This process of benzene treatment was repeated. After evaporation, the residue was treated with 100 ml. of benzene and was filtered. The filtrate was evaporated and the residue was triturated with 100 ml. of diethyl ether. The insoluble material was collected and was recrystallized from ethyl acetate to afford 1.0 g. of 2-ethylamino-6-methylnicotinic acid, m.p. 107°–110° C.

A stirred mixture of 0.5 g. of 2-ethylamino-6-methylnicotinic acid in 30 ml. of ethyl chloroformate was heated under reflux for 24 hours. The mixture was filtered and the filtrate was evaporated in a rotary evaporator. The residue was recrystallized from ethyl acetate (petroleum ether was added to initiate precipitation) to give 0.1 g. of 1-ethyl-7-methyl-2H-pyrido[2,3-d][1,3]oxazine-2,4[1H]-dione, m.p. 100°–12° C. (ref. Zalay et al., U.S. Pat. No. 3,838,120, m.p. 116°–17° C.).

To a solution of 0.046 g. (0.002 g. atom) of sodium in 20 ml. of ethanol was added 0.32 g. (0.002 mole) of diethyl malonate. After stirring for 5 minutes the solution was evaporated in a rotary evaporator. The residue was dissolved in 15 ml. of N,N-dimethylformamide and 0.2 g. (0.001 mole) of the previous compound was added. The mixture was heated under reflux for 1.5 hours. The mixture was cooled, diluted with a little water and was acidified with concentrated hydrochloric acid. The precipitate which formed was collected to give a few mg. of the title compound, m.p. 138°–40° C.

EXAMPLE 3

1-Ethyl-1,2-dihydro-4-hydroxy-7-methyl-2-oxo-1,8-naphthyridine-3-carboxylic acid ethyl ester sodium salt To a solution of 0.23 g. (0.01 g. atoms) of sodium in 100 ml. of ethanol was added 2.76 g. (0.01 mole) of 1-ethyl-1,2-dihydro-4-hydroxy-7-methyl-2-oxo-1,8-naphthyridine-3-carboxylic acid ethyl ester prepared by the method of Example 1. The mixture was stirred at room temperature for 2 hours. The mixture was filtered and the filter cake was dissolved in boiling ethanol. After cooling, the solution was diluted with diethyl ether to the cloudy point. Further cooling produced a precipitate which was collected to give 1.1 g. of the title compound, m.p. >300° C.

Anal. Calcd. for: $C_{14}H_{15}N_2O_4Na.\frac{1}{2}H_2O$: C, 54.72; H, 5.25; N, 9.12 Found: C, 54.64; H, 4.94; N, 9.17

EXAMPLE 4

1-Ethyl-1,2-dihydro-4-hydroxy-7-methyl-2-oxo-1,8-naphthyridine-3-carboxamide

A mixture of 1 g. of 1-ethyl-1,2-dihydro-4-hydroxy-7-methyl-2-oxo-1,8-naphthyridine-3-carboxylic acid ethyl ester (prepared as in Example 1) in 20 ml. of a saturated ethanolic ammonia solution was heated in an autoclave placed in a steam bath for 4 hours. The mixture was cooled and was filtered. The filter cake was triturated with 50 ml. of a 20% aqueous acetic acid solution. The insoluble material was collected, air dried and was recrystallized from ethanol to afford 0.4 g. of the title compound, m.p. 240°–2° C.

Anal. Calcd. for: $C_{12}H_{13}N_3O_3$: C, 58.29; H, 5.30; N, 17.00. Found: C, 57.92; H, 5.52; N, 16.91.

Percentage inhibition: 12%

EXAMPLE 5

1-Ethyl-1,2-dihydro-4-hydroxy-N-methyl-7-methyl-2-oxo-1,8-naphthyridine-3-carboxamide A stirred mixture of 4 g. of 1-ethyl-1,2-dihydro-4-hydroxy-7-methyl-2-oxo-1,8-naphthyridine-3-carboxylic acid ethyl ester (prepared as in Example 1) and 30 ml. of 40% aqueous methylamine in 20 ml. of methanol was heated under reflux for 5 hours. The solution was cooled, diluted with 100 ml. of water and was acidified with glacial acetic acid. The precipitate which formed was collected, air dried and was recrystallized from heptane to give 1.9 g. of the title compound, m.p. 150°–4° C.

Anal. Calcd. for $C_{13}H_{15}N_3O_3$: C, 59.76; H, 5.79; N, 16.08. Found: C, 59.49; H, 5.84; N, 15.85.

Percentage inhibition: 54%

EXAMPLE 6

1-Ethyl-1,2-dihydro-4-hydroxy-N-(2-methoxyethyl)-7-methyl-2-oxo-1,8-naphthyridine-3-carboxamide A stirred mixture of 1.38 g. (0.005 mole) of 1-ethyl-1,2-dihydro-4-hydroxy-7-methyl-2-oxo-1,8-naphthyridine-3-carboxylic acid ethyl ester (prepared as in Example 1) and 0.75 g. (0.01 mole) of 2-methoxyethylamine in 20 ml. of ethanol was heated under reflux for 5 hours. The solution was left at room temperature overnight. The precipitate which formed was collected and was stirred in 100 ml. of a 20% aqueous acetic acid solution for 30 minutes. The insoluble material was collected, air dried and was recrystallized from heptane to give 0.9 g. of the title compound, m.p. 118°-20° C.

Anal. Calcd. for $C_{15}H_{19}N_3O_4$: C, 59.00; H, 6.27; N, 13.76. Found: C, 58.68; H, 6.53; N, 13.70.

Percentage inhibition: 40%

EXAMPLE 7

1-Ethyl-1,2-dihydro-4-hydroxy-7-methyl-2-oxo-1,8-naphthyridine-3-carboxylic acid hydrazide A stirred mixture of 1.38 g. (0.005 mole) of 1-ethyl-1,2-dihydro-4-hydroxy-7-methyl-2-oxo-1,8-naphthyridine-3-carboxylic acid ethyl ester (prepared as in Example 1) and 0.32 g. (0.01 mole) of hydrazine in 30 ml. of ethanol was heated under reflux for 1 hour. The mixture was filtered and the filter cake was triturated with 100 ml. of 20% aqueous acetic acid. The insoluble material was collected, air dried and was recrystallized from ethanol to give 0.7 g. of the title compound, m.p. 211°-13° C.

Anal. Calcd. for $C_{12}H_{14}N_4O_3$: C, 54.95; H, 5.38; N, 21.37. Found: C, 54.75; H, 5.33; N, 21.32.

Percentage inhibition: 24%

EXAMPLE 8

1,7-Dimethyl-1,2-dihydro-4-hydroxy-2-oxo-1,8-naphthyridine-3-carboxylic acid ethyl ester To 10 g. (0.05 mole) of methyl 2-chloro-6-methylnicotinate in 50 ml. of methanol was added a chilled solution of 4 g. (0.13 mole) of methylamine in 25 ml. of methanol. This was placed in an autoclave and heated on a steam bath for 4 hours. The reaction was then stripped, added to water, made very basic with concentrated $NH_4OH$ and extracted once with $CHCl_3$. The $CHCl_3$ was washed once with water, dried and stripped giving 7 g. of a viscous liquid residue of 6-methyl-2-methylaminonicotinic acid, methyl ester. This product was then used directly without further purification.

To a solution of 9.0 g. (0.05 mole) of methyl 2-methylamino-6-methylnicotinate in 150 ml. of anhydrous diethyl ether was added 3.75 g. (0.025 mole) of ethyl malonyl chloride. The mixture was stirred at room temperature for 3 hours. The mixture was filtered and the filtrate was dissolved in 10 ml. of ethanol. This solution was added to a solution of 1.15 g. (0.05 g. atoms) of sodium in 75 ml. of ethanol. The mixture was stirred at room temperature for 5 minutes and was filtered. The filter cake was triturated with 100 ml. of water and this mixture was acidified with glacial acetic acid. The insoluble material was collected, air dried and was recrystallized from ethyl acetate to give 1.5 g. of the title compound, m.p. 143°-5° C.

Anal. Calcd. for $C_{13}H_{14}N_2O_4$: C, 59.53; H, 5.38; N, 10.68. Found: C, 59,83; H, 5.16; N, 10.78.

Percetate inhibition: 51%

EXAMPLE 9

1,2-dihydro-4-hydroxy-7-methyl-2-oxo-1-propyl-1,8-naphthyridine-3-carboxylic acid ethyl ester A stirred mixture of 37.1 g. (0.2 mole) of methyl 2-chloro-6-methyl-nicotinate, 11.8 g. (0.02 mole) of propylamine and 21.2 g. (0.02 mole) of sodium carbonate in 200 ml. of ethanol was heated under reflux for 5 hours. The mixture was filtered and the filtrate was evaporated in a rotary evaporator. The residue was triturated with 200 ml. of water and was extracted with 100 ml. of diethyl ether. The ether layer was dried over magnesium sulfate, filtered and was evaporated to give 31 g. of an oil. A small amount of this oil was dissolved in diethyl ether and was acidified with an etheral hydrochloric acid solution. On cooling, the oil which separated crystallized to yield 6-methyl-2-propylaminonicotinic acid methyl ester, hydrochloride. The solid was collected and was recrystallized from ethyl acetate to give the analytical sample, m.p. 113°-15° C.

Anal. Calcd. for $C_{11}H_{17}ClN_2O_2$: C, 53.99; H, 7.00; N, 11.45. Found: C, 53.50; H, 7.12; N, 11.53.

To a solution of 30.7 g. (0.015 mole) of methyl-2-propylaminonicotinic acid methyl ester in 250 ml. of anhydrous diethyl ether was added 11.25 g. (0.0075 mole) of ethyl malonyl chloride. The mixture was stirred at room temperature for 2 hours. The mixture was filtered and the filtrate was evaporated in a rotary evaporator. The residue was dissolved in 20 ml. of ethanol and this solution was added to a solution of 3.4 g. (0.015 g. atom) of sodium in 200 ml. of ethanol. After stirring at room temperature for 5 minutes, the mixture was diluted with water and was acidified with concentrated hydrochloric acid. The precipitate which formed was collected, air dried and was recrystallized from heptane to afford 3.4 g. of the title compound, m.p. 128°-30° C.

Anal. Calcd. for $C_{15}H_{18}N_2O_4$: C, 62.05; H, 6.25; N, 9.65 Found: C, 61.90; H, 6.24; N, 9.63

Percentage inhibition: 59%

EXAMPLE 10

1-Allyl-1,2-dihydro-4-hydroxy-7-methyl-2-oxo-1,8-naphthyridine-3-carboxylic acid ethyl ester A stirred mixture of 9.25 g. (0.05 mole) of methyl 2-chloro-6-methylnicotinate, 2,85 g. (0.05 mole) of allylamine and 5.3 g. (0.05 mole) of sodium carbonate in 50 ml. of ethanol was heated under reflux for 5 hours. The mixture was filtered and the filtrate was evaporated in a rotary evaporator. The residue was diluted with 50 ml. of water and was extracted with 50 ml. of diethyl ether. The ether layer was dried over magnesium sulfate, filtered and was evaporated. The residue was passed through a neutral aluminum oxide column using ethyl acetate as the eluent. Evaporation of the ethyl acetate gave 3.1 g. of product. A small amount of this oil was dissolved in diethyl ether containing a few drops of ethanol and this solution was acidified with an ethereal hydrochloric acid solution. The precipitate which formed was collected and was recrystallized from ethyl acetate to give 2-allylamino-6-methylnicotinic acid methyl ester, m.p. 140°-2° C.

Anal. Calcd. for $C_{11}H_{15}ClN_2O_2.\frac{1}{2}H_2O$: C, 52.49; H, 6.42; N, 11.13. Found: C, 52.96; H, 5.94; N, 11.26.

To a solution of 2.88 g. (0.015 mole) of 2-allylamino-6-methylnicotinic acid, methyl ester in 50 ml. of anhydrous diethyl ether was added 1.12 g. (0.0075 mole) of ethyl malonyl chloride. The mixture was stirred at room temperature for 4 hours. The mixture was filtered and the filtrate was evaporated in a rotary evaporator. The residue was dissolved in 5 ml. of ethanol and this solution was added to a solution of 0.23 g. (0.01 g. atoms) of sodium in 20 ml. of ethanol. The mixture was stirred at room temperature for 5 minutes. The mixture was diluted with water and was acidified with glacial acetic acid. The mixture was extracted with diethyl ether and the ether layer was dried over magnesium sulfate, filtered and was acidified with an etheral hydrochloric acid solution. The mixture was filtered and the filtrate was evaporated. The residue was recrystallized from heptane to give 10 mg. of the title compound, m.p. 110°–112° C.

Anal. Calcd. for $C_{15}H_{16}N_2O_4$: C, 62.49; H, 5.59; N, 9.72. Found: C, 62.22; H, 5.49; N, 9.62.

Percentage inhibition: 23%

EXAMPLE 11

1-Benzyl-1,2-dihydro-4-hydroxy-7-methyl-2-oxo-1,8-naphthyridine-3-carboxylic acid, ethyl ester To 15 g. (0.081 mole) of methyl 2-chloro-6-methylnicotinate in methanol was added 17.3 g. (0.162 mole) of benzylamine and this mixture was refluxed for 5 hours. The reaction was then stripped, added to water, made very basic via $NH_4OH$, extracted into $CHCl_3$, rinsed with water, dried and stripped. Chilling and scratching produced 4 g. of a solid 2-benzylamino-6-methylnicotinic acid, methyl ester that was filtered off and rinsed with petroleum ether, m.p. 76°–80° C. Recrystallized from ethanol-m.p. 84°–88° C.

Anal. Calcd. for $C_{15}H_{16}N_2O_2$: C, 70.29; H, 6.29; N, 10.93. Found: C, 70.43; H, 6.32; N, 10.95.

To a solution of 3.6 g. (0.014 mole) of methyl 2-benzylamino-6-methylnicotinate in 50 ml. of anhydrous diethyl ether was added 1.05 g. (0.007 mole) of ethyl malonyl chloride. The mixture was stirred at room temperature for 3 hours. The mixture was filtered and the filtrate was evaporated in a rotary evaporator. The residue was dissolved in 5 ml. of ethanol and this solution was added to a solution of 0.32 g. (0.014 g. atoms) of sodium in 50 ml. of ethanol. After stirring at room temperature for 5 minutes, the mixture was diluted with water and was acidified with glacial acetic acid. The precipitate which formed was collected, air dried and was crystallized from ethanol to give 0.9 g. of the title compound, m.p. 155°–7° C.

Anal. Calcd. for $C_{19}H_{18}N_2O_4$: C, 67.44; H, 5.36; N, 8.28 Found: C, 67.22; H, 5.41; N, 8.25

Percentage inhibition: 30%

EXAMPLE 12

1-Ethyl-1,2-dihydro-4-hydroxy-2-oxo-1,8-naphthyridine-3-carboxylic acid, ethyl ester To a cold diethyl ether solution containing about 2.8 g. (0.067 mole) of diazomethane generated from 10 g. of nitrosomethyl urea and 30 cc. of 40% potassium hydroxide (see Organic Synthesis, Col. 1, Vol. II, page 166) was added in portions 9.45 g. (0.06 mole) of 2-chloronicotinic acid. After the evolution of nitrogen had ceased the reaction mixture was allowed to stand at room temperature overnight. The solvent was removed in a rotary evaporator leaving 2-chloro-nicotinic acid, methyl ester as a residual oil whose infrared spectrum indicated no OH absorption was present. The oil was used directly in the next step. The above compound has also been described by F. G. Mann and J. A. Reid, J. Chem. Soc., 1952, 2057.

To 10 g. (0.06 mole) of methyl 2-chloronicotinate in 50 ml. of methanol was added 6.0 g. (0.13 mole) of ethylamine in 25 ml. of methanol and this was placed into an autoclave and heated on a steam bath for 4 hours. Then the reaction solution was stripped, water added, made very basic via $NH_4OH$, extracted into $CHCl_3$, washed with water, dried and then stripped to dryness to yield 2-ethylaminonicotinic acid, methyl ester. An HCl-salt was prepared by adding the crude residue to ethyl acetate and then adding ethereal-HCl. The product precipitated out of solution and was collected on a filter and rinsed with petroleum ether to give 7 g. of product with a m.p. of 140°–5° C.

Anal. Calcd. for $C_9H_{13}N_2ClO_2$: C, 49.88; H, 6.05; N, 12.93. Found: C, 49.85; H, 6.05; N, 13.08.

To a solution of 9.0 g. (0.05 mole) of methyl 2-ethylaminonicotinate in 400 ml. of anhydrous diethyl ether was added 3.75 g. (0.25 mole) of ethyl malonyl chloride. The mixture was stirred at room temperature for 3 hours and was then filtered. The filtrate was evaporated in a rotary evaporator and the residue was dissolved in 15 ml. of ethanol and this solution was added to a solution of 1.15 g. (0.05 g. atoms) of sodium in 150 ml. of ethanol. The mixture was stirred at room temperature for 10 minutes. The mixture was diluted with water to the cloudy point and was then acidified with glacial acetic acid. The precipitate which formed was collected, air dried and was recrystallized from heptane to give 0.7 g. of the title compound, m.p. 122°–5° C.

Anal. Calcd. for $C_{13}H_{14}N_2O_4$: C, 59.53; H, 5.38; N, 10.68. Found: C, 59.41; H, 5.33; N, 10.66.

Percentage inhibition: 35%

EXAMPLE 13

1-Ethyl-1,2-dihydro-4-hydroxy-2-oxo-1,8-naphthyridine-3-carboxylic acid, ethyl ester To a suspension of 25 g. of 2,3-pyridinedicarboxylic anhydride in 350 ml. of methyl ethyl ketone was bubbled a stream of ammonia gas for 15 minutes. The mixture was filtered and the filter cake was dissolved in 250 ml. of water. To this solution was bubbled a stream of sulfur dioxide. The precipitate which formed was collected to give 9.0 g. of 2-carbamylnicotinic acid, m.p. 178°–82° C. dec. (Ref. Mann et al., J. Chem. Soc., 2057 (1952); m.p. 172° C. dec.).

To a suspension of 2.0 g. of 2-carbamylnicotinic acid in 20 ml. of N,N-dimethylformamide was added 5.5 g. of lead tetra-acetate. The mixture was stirred at a temperature of 50°–60° C. for 1 hour. The mixture was poured into 20 ml. of water. The precipitate was collected to give 0.65 g. of 2H-pyrido[2,3-d][1,3]oxazine2,4[1H]dione, 224°–6° C. dec. (Ref. Beckwith et al., J. Chem. Soc., (C) 2756 (1969); m.p. 217°–19° C.).

To 20 ml. of dry N,N-dimethylformamide was added 0.19 g. (0.004 mole) of 50% sodium hydride. Then a suspension of 0.65 g. (0.004 mole) of 2H-pyrido[2,3-d][1,3]oxazine-2,4[1H]dione in 10 ml. of N,N-dimethylformamide was added. After 0.248 g. (0.008 mole) of ethyl iodide was added the mixture was stirred at room temperature for 2 hours. The mixture was slowly diluted with water and the precipitate which formed was collected, air dried, and was recrystallized from ethanol to give 0.2 g. of 1-ethyl-2H-pyrido[2,3-d]-[1,3]oxazine-2,4[1H]dione, m.p. 143°–5° C.

Anal. Calcd. for $C_9H_8N_2O_3$: C, 56.25; H, 4.20; N, 14.58. Found: C, 56.19; H, 4.25; N, 14.61.

To a solution of 0.115 g. (0.005 g. atom) of sodium in 20 ml. of ethanol was added 1.6 g. (0.01 mole) of diethyl malonate. After stirring for 5 minutes the solution was evaporated in a rotary evaporator. The residue was dissolved in 15 ml. of N,N-dimethylformamide and 0.96 g. (0.005 mole) of 1-ethyl-2H-pyrido[2,3-d]-[1,3]oxazine-2,4[1H]dione was added. The mixture was heated under reflux for 1.5 hours. The mixture was cooled, diluted with a little water and was acidified with concentrated hydrochloric acid. The precipitate which formed was collected, air dried and was recrystallized from heptane to give 0.2 g. of the title product, m.p. 120°–2° C.

EXAMPLE 14

1-Ethyl-1,2-dihydro-4-ethoxy-7-methyl-2-oxo-1,8-naphthyridine-3-carboxylic acid, ethyl ester A stirred mixture of 1 g. of 1-ethyl-1,2-dihydro-4-hydroxy-7-methyl-2-oxo-1,8-naphthyridine-3-carboxylic acid ethyl ester in 20 ml. of thionyl chloride was heated under reflux for 3 hours. The thionyl chloride was removed in a rotary evaporator and the residue was recrystallized from ethyl acetate to give 0.3 g. of 1-ethyl-1,2-dihydro-4-chloro-7-methyl-2-oxo-1,8-naphthyridine-3-carboxylic acid ethyl ester, m.p. 143°–5° C.

Anal. Calcd. for $C_{14}H_{15}ClN_2O_3$: C, 57.05; H, 5.13; N, 9.51. Found: C, 57.21; H, 4.93; N, 9.55.

To a solution of 0.11 g. (0.005 g. atoms) of sodium in 20 ml. of ethanol was added 1.47 g. (0.005 mole) of 1-ethyl-1,2-dihydro-4-chloro-7-methyl-2-oxo-1,8-naphthyridine-3-carboxylic acid, ethyl ester. The mixture was heated under reflux for 4 hours. The mixture was cooled and was diluted with water. The precipitate which formed was collected, air dried and was recrystallized from heptane to give 0.5 g. of the title compound, m.p. 77°–9° C.

Anal. Calcd. for $C_{16}H_{20}N_2O_4$: C, 63.14; H, 6.62; N, 9.21. Found: C, 63.17; H, 6.68; N, 9.17.

Percentage inhibition: 62%

EXAMPLE 15

1-Ethyl-1,2-dihydro-4-hydroxy-7-methyl-2-oxo-1,8-naphthyridine-3-carbonitrile

A stirred mixture of 10 g. of 1-ethyl-1,2-dihydro-4-hydroxy-7-methyl-2-oxo-1,8-naphthyridine-3-carboxamide (prepared as in Example 4) in 200 ml. of phosphorus oxychloride was heated under reflux for 3 hours. The phosphorus oxychloride was evaporated in a rotary evaporator. To this residue was quickly added 400 ml. of ice water. The insoluble material was collected, air dired and was recrystallized from ethanol to give 5.5 g. of 4-chloro-1-ethyl-1,2-dihydro-7-methyl-2-oxo-1,8-naphthyridine-3-carbonitrile, m.p. 215°–17° C.

Anal. Calcd. for $C_{12}H_{10}ClN_3O$: C, 58.19; H, 4.07; N, 16.96. Found: C, 57.93; H, 4.24; N, 16.81.

A stirred mixture of 7.41 g. (0.03 mole) of 4-chloro-1-ethyl-1,2-dihydro-7-methyl-2-oxo-1,8-naphthyridine-3-carbonitrile, 2.13 g. (0.03 mole) of pyrrolidine and 3.18 g. (0.03 mole) of sodium carbonate in 100 ml. of ethanol was heated under reflux for 1 hour. The mixture was filtered and the filter cake was triturated with 200 ml. of water. The insoluble material was collected, air dried and was recrystallized from 2-ethoxyethanol to give 7.4 g. of 1-ethyl-1,2-dihydro-7-methyl-2-oxo-4-(1-pyrrolidinyl)-1,8-naphthyridine-3-carbonitrile, m.p. 211°–13° C.

Anal. Calcd. for $C_{16}H_{18}N_4O$: C, 68.06; H, 6.43; N, 19.85. Found: C, 68.24; H, 6.57; N, 19.84.

A stirred mixture of 0.5 g. of 1-ethyl-1,2-dihydro-7-methyl-2-oxo-4-(1-pyrrolidinyl)-1,8-naphthyridine-3-carbonitrile in 15 ml. of 20% aqueous sodium hydroxide containing 15 ml. of ethanol was heated under reflux for 3 hours. The solution was cooled and was acidified with concentrated hydrochloric acid. The precipitate which formed was collected, air dried and was recrystallized from ethanol to afford 0.2 g. of the title compound, m.p. 274°–6° C.

Anal. Calcd. for $Cl_2H_{11}N_3O_2$: C, 62.87; H, 4.84; N, 18.33. Found: C, 62.62; H, 4.61; N, 17.97.

Percentage inhibition: 39%

EXAMPLE 16

1-Ethyl-1,2-dihydro-4-hydroxy-7-methyl-2-oxo-1,8-naphthyridine-3-carboxylic acid A stirred mixture of 1 g. of 1-ethyl-1,2-dihydro-4-ethoxy-7-methyl-2-oxo-1,8-naphthyridine-3-carboxylic acid ethyl ester (prepared as in Example 14) in 15 ml. of 20% aqueous sodium hydroxide containing 5 ml. of ethanol was heated under reflux for 4 hours. The mixture was cooled and was acidified with glacial acetic acid and was diluted with water. The precipitate which formed was collected, air dried and was recrystallized from ethanol to afford 0.3 g. of the title compound, m.p. 162°–5° C.

Anal. Calcd. for $C_{12}H_{12}N_2O_4$: C, 58.06; H, 4.87; N, 11.29. Found: C, 57.76; H, 4.94; N, 11.22.

Percentage inhibition: 56%

EXAMPLE 17

1-Ethyl-1,2-dihydro-4-hydroxy-7-methyl-2-oxo-1,8-naphthyridine

A stirred mixture of 0.5 g. of 1-ethyl-1,2-dihydro-4-hydroxy-7-methyl-2-oxo-1,8-naphthyridine-3-carboxylic acid ethyl ester was heated under reflux for 5 hours in 20 ml. of a 20% sodium hydroxide solution was cooled and was acidified with glacial acetic acid. The precipitate which formed was collected, air dried and was recrystallized from ethanol to give 0.2 g. of the title compound, m.p. 320°–3° C. dec.

Anal. Calcd. for $C_{11}H_{12}N_2O_2$: C, 64.69; H, 5.92; N, 13.72. Found: C, 64.47; H, 5.99; N, 13.59.

Percentage inhibition: 33@16 mg/kg.

EXAMPLE 18

1,2-dihydro-4-hydroxy-7-methyl-2-oxo-1,8-naphthyridine-3-carboxylic acid ethyl ester A mixture of 5 g. of 2-chloro-6-methylnicotinic acid methyl ester and 1 g. of ammonia in 25 ml. of methanol was heated in an autoclave in a steam bath for 10 hours. The mixture was evaporated in a rotary evaporator, diluted with water and was basified with concentrated ammonium hydroxide. The mixture was extracted with diethyl ether. The ether layer was dried over magnesium sulfate, filtered and was evaporated to give about 2.5 g. of 2-amino-6-methylnicotinic acid methyl ester as an oil which was used in the next step without further purification.

To a solution of 7.9 g. (0.047 mole) of methyl 2-amino-6-methyl-nicotinate in 250 ml. of anhydrous diethyl ether was added 3.5 g. (0.0235 mole) of ethyl malonyl chloride. The mixture was stirred at room temperature for 4 hours. The mixture was filtered and the filtrate was evaporated in a rotary evaporator. The residue was triturated with 25 ml. of cold ethanol. The insoluble material was collected and was recrystallized from heptane to yield 1.8 g. of 2-[(3-ethoxy-1,3-dioxopropyl)amino]-6-methyl-3-pyridine carboxylic acid ethyl ester, m.p. 92°–5° C.

Anal. Calcd. for $C_{14}H_{18}N_2O_5$: C, 57.13; H, 6.17; N, 9.52. Found: C, 57.18; H, 6.20; N, 9.51.

The filtrate from the previous reaction was added to a solution of 1.08 g. (0.047 g. atom) of sodium in 150 ml. of ethanol. The mixture was stirred for 5 minutes and was diluted with water and was acidified with glacial acetic acid. The precipitate which formed was collected, air dried and was recrystallized from ethanol to afford 0.2 g. of the title compound, m.p. 190°–3° C.

Anal. Calcd. for $C_{12}H_{12}N_2O_4$: C, 58.06; H, 4.87; N, 11.29. Found: C, 57.64; H, 4.89; N, 11.20.

What is claimed is:

1. A process for treating peptic ulcer disease which comprises orally or parenterally administering to a mammal in need thereof an anti-secretory amount of a compound of the formula:

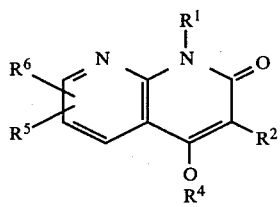

in which
   $R^1$ is hydrogen, alkyl of 1 to 6 carbon atoms, aralkyl of 7 to 9 carbon atoms, or alken-(3,4,5 or 6)-yl of 3 to 6 carbon atoms;
   $R^2$ is hydrogen, alkoxycarbonyl of 2 to 7 carbon atoms; carboxy, carbamyl, N-alkylcarbamyl of 2 to 7 carbon atoms, N-alkoxyethylcarbamyl of 4 to 9 carbon atoms, hydrazido or cyano;
   $R^4$ is hydrogen, alkyl of 1 to 6 carbon atoms;
   $R^5$ and $R^6$ are independently hydrogen or alkyl of 1 to 6 carbon atoms
or a pharmaceutically acceptable alkali metal salt thereof.

2. The process of claim 1 in which said compound is 1-ethyl-1,2-dihydro-4-hydroxy-7-methyl-2-oxo-1,8-naphthyridine-3-carboxylic acid ethyl ester.

3. The process of claim 1 in which said compound is 1-ethyl-1,2-dihydro-4-hydroxy-7-methyl-2-oxo-1,8-naphthyridine-3-carboxylic acid ethyl ester sodium salt.

4. The process of claim 1 in which said compound is 1-ethyl-1,2-dihydro-4-hydroxy-7-methyl-2-oxo-1,8-naphthyridine-3-carboxamide.

5. The process of claim 1 in which said compound is 1-ethyl-1,2-dihydro-4-hydroxy-N-methyl-7-methyl-2-oxo-1,8-naphthyridine-3-carboxamide.

6. The process of claim 1 in which said compound is 1-ethyl-1,2-dihydro-4-hydroxy-N-(2-methoxyethyl)-7-methyl-2-oxo-1,8-naphthyridine-3-carboxamide.

7. The process of claim 1 in which said compound is 1-ethyl-1,2-dihydro-4-hydroxy-7-methyl-2-oxo-1,8-naphthyridine-3-carboxylic acid hydrazide.

8. The process of claim 1 in which said compound is 1,7-dimethyl-1,2-dihydro-4-hydroxy-2-oxo-1,8-naphthyridine-3-carboxylic acid ethyl ester.

9. The process of claim 1 in which said compound is 1,2-dihydro-4-hydroxy-7-methyl-2-oxo-1-propyl-1,8-naphthyridine-3-carboxylic acid ethyl ester.

10. The process of claim 1 in which said compound is 1-allyl-1,2-dihydro-4-hydroxy-7-methyl-2-oxo-1,8-naphthyridine-3-carboxylic acid ethyl ester.

11. The process of claim 1 in which said compound is 1-benzyl-1,2-dihydro-4-hydroxy-7-methyl-2-oxo-1,8-naphthyridine-3-carboxylic acid, ethyl ester.

12. The process of claim 1 in which said compound is 1-ethyl-1,2-dihydro-4-hydroxy-2-oxo-1,8-naphthyridine-3-carboxylic acid, ethyl ester.

13. The process of claim 1 in which said compound is 1-ethyl-1,2-dihydro-4-ethoxy-7-methyl-2-oxo-1,8-naphthyridine-3-carboxylic acid, ethyl ester.

14. The process of claim 1 in which said compound is 1-ethyl-1,2-dihydro-4-hydroxy-7-methyl-2-oxo-1,8-naphthyridine-3-carbonitrile.

15. The process of claim 1 in which said compound is 1-ethyl-1,2-dihydro-4-hydroxy-7-methyl-2-oxo-1,8-naphthyridine-3-carboxylic acid.

16. The process of claim 1 in which said compound is 1-ethyl-1,2-dihydro-4-hydroxy-7-methyl-2-oxo-1,8-naphthyridine.

17. The process of claim 1 in which said compound is 1,2-dihydro-4-hydroxy-7-methyl-2-oxo-1,8-naphthyridine-3-carboxylic acid ethyl ester.

* * * * *